United States Patent [19]

Bezuidenhout et al.

[11] Patent Number: 6,100,427
[45] Date of Patent: Aug. 8, 2000

[54] PRODUCTION OF AMIDES AND/OR ACIDS FROM NITRILES

[75] Inventors: Barend Christiaan Buurman Bezuidenhout, Sasolburg; Zamile Denga, Johannesburg; Rian Steyn, Kempton Park; Petrus Johannes Steynberg, Sasolburg; Nicolaus Ladislaus Stark, Vanderbijlpark, all of South Africa

[73] Assignee: Catalytic Distillation Technologies, Pasadena, Tex.

[21] Appl. No.: 09/183,052

[22] Filed: Oct. 30, 1998

[30] Foreign Application Priority Data

Oct. 30, 1997 [ZA] South Africa .......................... 97/9772

[51] Int. Cl.[7] .......................... C07C 231/06; C07C 51/08
[52] U.S. Cl. .............................. 564/127; 203/31; 203/96; 562/407; 562/408; 562/526; 564/126; 564/128
[58] Field of Search ........................ 203/31, 96; 562/407, 562/408, 526; 564/126, 127, 128

[56] References Cited

U.S. PATENT DOCUMENTS

| | | | |
|---|---|---|---|
| 3,920,670 | 11/1975 | Norton | 546/319 |
| 3,928,442 | 12/1975 | Seale et al. | 564/127 |
| 3,962,333 | 6/1976 | Yoshimura et al. | 564/127 |
| 4,000,195 | 12/1976 | Svarz et al. | 564/127 |

*Primary Examiner*—Johann Richter
*Assistant Examiner*—Brian J. Davis
*Attorney, Agent, or Firm*—Kenneth H. Johnson

[57] ABSTRACT

A process for producing an amide and/or acid from a nitrile comprises introducing a nitrile, as a first reactant, and a hydration compound, as a second reactant which is capable of reacting with the nitrile to convert it to its corresponding amide thus hydrating the nitrile and/or to convert it to its corresponding acid, into a treatment zone. The nitrile is subjected to catalytic distillation in the treatment zone in the presence of the hydration compound, to hydrate at least some of the nitrile to the corresponding amide and/or to form its corresponding acid. The amide and/or acid is withdrawn from the treatment zone.

13 Claims, 1 Drawing Sheet

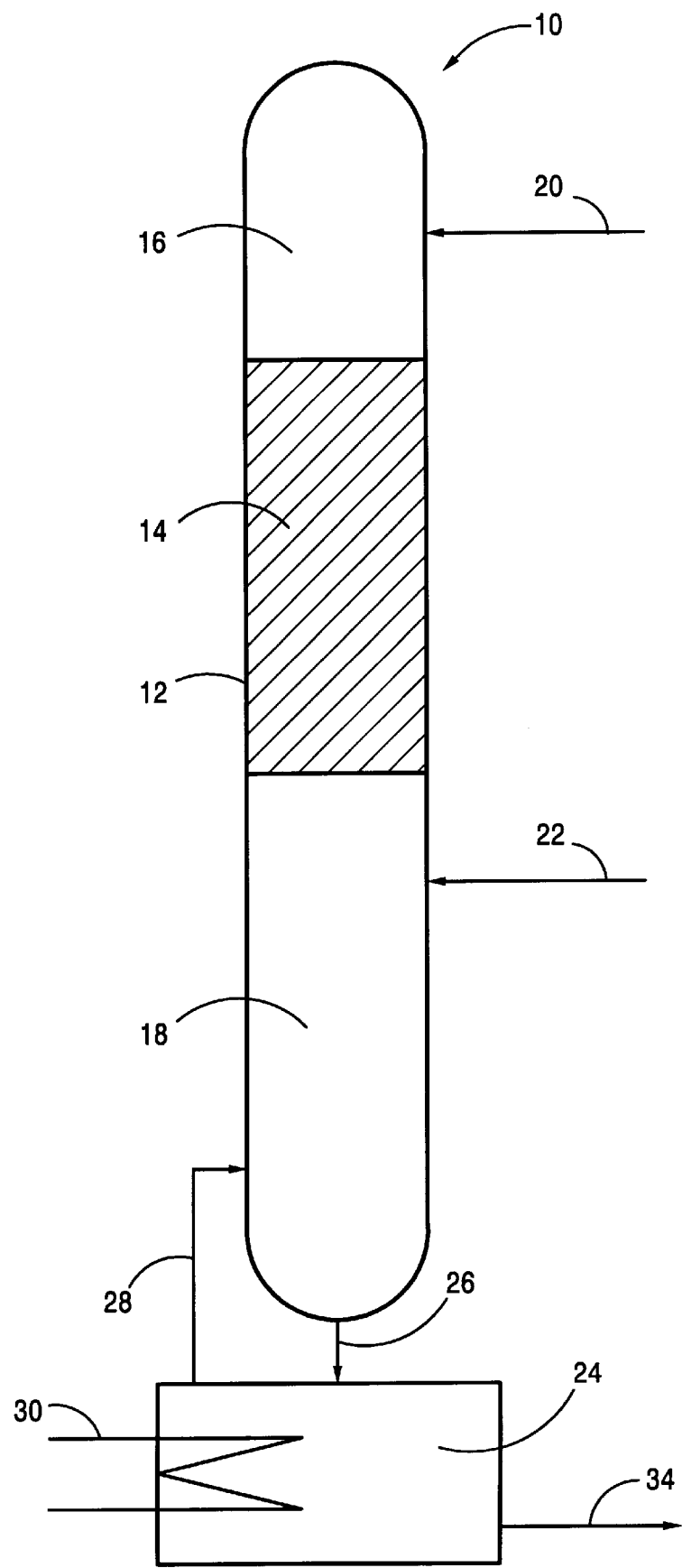

PRODUCTION OF AMIDES AND/OR ACIDS FROM NITRILES

This invention relates to the production of amides and/or acids from nitriles. It relates in particular to a process for producing an amide and/or acid from a nitrile.

SUMMARY OF THE INVENTION

According to the invention, there is provided a process for producing an amide and/or acid from a nitrile, which process comprises introducing a nitrile, as a first reactant, and a hydration compound, as a second reactant which is capable of reacting with the nitrile to convert it to its corresponding amide thus hydrating the nitrile and/or to convert it to its corresponding acid, into a treatment zone; subjecting the nitrile to catalytic distillation in the treatment zone in the presence of the hydration compound, to hydrate at least some of the nitrile to the corresponding amide and/or to form its corresponding acid; and withdrawing the amide and/or acid from the treatment zone.

Catalytic distillation thus involves effecting a chemical reaction simultaneously with or in combination with distillation, in a single treatment zone. The treatment zone will thus comprise at least one reaction zone in which the hydration reaction of the nitrile to the amide and/or acid takes place catalytically in the presence of a catalyst, and at least one distillation zone adjacent the reaction zone in which distillation of the reaction product(s) from the reaction zone and/or unreacted reactants, takes place.

The reaction zone may thus comprise a packed bed of catalyst particles capable of catalyzing the conversion or hydration of the nitrile to its corresponding amide. Any suitable hydration catalyst can be used, typically a copper or copper-based hydration catalyst, e.g. a copper-chromium or a copper oxide hydration catalyst.

The first reactant may comprise an unsaturated or aromatic nitrile, such as acrylonitrile, methacrylonitrile, crotononitrile, allyl cyanide, or benzonitrile, which will thus be hydrated to the corresponding unsaturated or aromatic amide and/or acid, without a substantial degree of polymerization taking place. Instead, however, the first reactant may comprise a saturated nitrile such as acetonitrile, propionitrile, butyronitrile, or isobutyronitrile.

The treatment zone will typically be provided in a column or tower, with the catalyst bed provided in a section of the tower. The distillation zone may thus be provided above and/or below the catalyst bed. Preferably, a distillation zone is provided above and below the catalyst bed. Suitable packed distillation media, e.g. Raschig rings, or distillation apparatus or equipment, are then provided in the column below and/or above the catalyst bed, i.e. in the distillation zone(s).

The process may include boiling a liquid component in a reboiling zone operatively connected to a lower end of the treatment zone, to provide the driving force for the catalytic distillation. A portion of the liquid component may then, if desired, be introduced into the treatment zone, e.g. above or below the catalyst bed.

The liquid component may be such that it does not partake in the hydration reaction i.e. it only provides the driving force for the catalytic distillation and thus assists in distillation of the reactants and products in the treatment zone. In such case, the second reactant may be fed into the treatment zone at a location spaced from the point of introduction of the first reactant or nitrile into the treatment zone, e.g. above the catalyst bed when the nitrile is fed into the treatment zone below the catalyst bed. The second reactant must thus be capable of hydrating the nitrile at the conditions prevailing in the treatment zone and in the presence of the catalyst. In particular, the second reactant may be water.

The liquid component may be an organic compound such as an alcohol, an aromatic or a paraffin.

However, the liquid component may, instead, be such that it partakes in the hydration reaction. It may thus, in particular, be the same as the second reactant. In other words, some second reactant is then used for reboiling, while some thereof is introduced into the treatment zone as hereinbefore described.

The higher boiling of the first and second reactants may be introduced into the treatment zone above the catalyst bed, with the lower boiling being introduced below or above the catalyst bed. In the event that the first reactant or nitrile is the higher boiling component, a portion thereof will thus be introduced above the catalyst bed, while remainder thereof will be boiled in the boiling zone to provide the driving force for the catalytic distillation.

The withdrawal of the amide may be effected as an overhead or distillate component at the top of the treatment zone or as a high boiling component at the bottom of the treatment zone, e.g. from the reboiling zone, depending on the relative boiling points of the first and second reactants.

The column may be of any desired length and width, and is typically in the region of 10 m to 60 m long. Typically, its diameter is in the region of 25 mm to 110 mm on a pilot plant scale and greater than 10 m for a commercial scale operation. The catalyst bed may also be of any desired length, e.g. 0.5–10 m. The pressure in the column can vary widely, e.g. between 10 kPa(g) and 10000 kPa(g), and can be controlled by means of an inert gas such as nitrogen or argon. The pressure, and hence the reaction temperature, in the column will determine the product produced. Thus, if an amide corresponding to the nitrile which is fed into the column, is produced at a given column pressure and hence a specific reaction temperature, the corresponding acid can instead, or additionally, be produced by increasing the column pressure and hence the reaction temperature at which the reaction is effected, so that over or excessive hydrolysis is effected, thereby forming the corresponding acid.

BRIEF DESCRIPTION OF THE DRAWING

The figure is a diagrammatic drawing which shows a simplified flow diagram of a process according to the invention.

DETAILED DESCRIPTION

The invention will now be described in more detail, with reference to the accompanying diagrammatic drawing which shows a simplified flow diagram of a process according to the invention for producing an amide and/or an acid from a nitrile, as well as the subsequent non-limiting Examples.

In the drawing, reference numeral 10 generally indicates a process according to the invention for producing an amide from a nitrile.

The process 10 includes a catalytic distillation column 12. The dimensions of the column 12 can vary widely, but it is typically about 10 m long with an internal diameter of 25 mm.

A reaction zone 14 is provided inside the column 12 such that a distillation zone 16 is provided above the zone 14 while another distillation zone 18 is provided below the reaction zone 14. The reaction zone 14 comprises a supported bed of a copper based particulate hydration catalyst such as a supported copper-chromium catalyst, a supported copper oxide catalyst or another similar hydration catalyst. The distillation zones 16, 18 are packed with Raschig rings (not shown).

A water feedline 20 leads into the column 12 above the bed 14, while a nitrile feedline 22 leads into the column 12 immediately below the bed 14. However, it is to be appreciated that the nitrile feedline 22 can also lead into the column 12 above the bed 14.

A reboiler 24 is located below the column 12. A withdrawal line 26 leads from the bottom of the column 12 to the reboiler 24, while a return line 28 leads from the reboiler 24 back to the column 12. The reboiler 24 is fitted with a heater 30, while a product withdrawal line 34 leads from the reboiler.

In use, sufficient water is introduced into the reboiler 24 to fill it to 30–80% of its volumetric capacity, and heated. The pressure in the column 12 is regulated at between 0.1 and 100 bar, as desired, by means of an inert gas such as nitrogen or argon. The water in the reboiler 24 is boiled up into the column 12 until full reflux is reached. At that stage, a feedstream of a nitrile, such as acrylonitrile which has a lower boiling point than water, is introduced into the column 22 along the feedline 22, typically at the rate of between 0.001 and 50 kg per hour, followed by the introduction of water along the flowline 20 at a suitable feed rate, e.g. between 0.001 and 100 kg per hour. Typically, the nitrile used as feedstock is stabilized against polymerization with radical inhibitors such as hydroquinone or methylated hydroquinone, before introduction thereof into the column. The column 12 is kept under conditions of reflux, and an amide product of the nitrile, together with excess water, is recovered as the bottom stream along the flowline 34, at a rate of 0.002 kg to 150 kg per hour.

In simulations of the process 10, the following non-limiting examples was conducted in the laboratory.

EXAMPLE 1

Pellets of a copper-chromite catalyst in its reduced form (650 g), supported in stainless steel wire socks (22 in number), were packed in a 5 m section of a catalytic distillation column 12 having dimensions of 10 m height×25 mm diameter. The top one meter of the column (zone 16) and the bottom 4 meters (zone 18) were filled with Raschig rings. Demineralized water was introduced into the reboiler 24 to 30% of its capacity. Under a nitrogen atmosphere, the water was boiled up into the column under atmospheric pressure (85 kPa) until a reflux was reached (96° C.). Acrylonitrile containing 35 ppm methylated hydroquinone (MeHQ) was introduced at a feed point (flow line 22) just below the catalyst bed at a rate of 30 g/hour and water fed (flow line 20) above the catalyst zone at a rate of 84 g/hour. After the introduction of acrylonitrile, the temperature inside the catalyst bed dropped to the boiling point of the acrylonitrile-water azeotrope (64° C.). The product solution containing 35% by weight acrylamide (100% conversion and 100% selectivity) was removed from the reboiler along the flow line 34, at a rate of 114 g/hour.

EXAMPLE 2

Extrudates or pellets of a copper oxide or copper-chromite catalyst in reduced form (350 g), supported in stainless steel wire socks (10 in number) and wrapped in demister wire, were packed in the top section of a glass catalytic distillation column having dimensions of 2.1 m height×35 mm diameter. The bottom 600 mm of the column was filled with Raschig rings or structured distillation packing. De-aerated demineralized water was introduced into the reboiler to 30% of its capacity. Under a nitrogen atmosphere, the water was boiled up into the column under atmospheric pressure (85 kPa), until reflux was reached (96° C.). De-aerated nitrile was introduced at a feed point just below the catalyst bed at a rate of 10–25 g/hour, and water was fed into the column above the catalyst zone at the rate required to produce the desired product concentration. After the introduction of the nitrile, the temperature inside the catalyst bed decreased to the boiling point of the nitrile-water azeotrope. The product solution (25–130 g/h) containing up to 50% by weight of the amide (>90% conversion and selectivity) was removed from the reboiler.

EXAMPLE 3

Extrudates of a copper oxide catalyst in its reduced form (900 g), supported in stainless steel wire socks (22 in number) and wrapped in demister wire, were packed in a 8.5 m section of a catalytic distillation column having dimensions of 10 m height×25 mm diameter. The bottom 1.5 m of the column was filled with 10 mm Berl saddles. De-aerated demineralized water was introduced into the reboiler to 30% of its capacity. Under a nitrogen atmosphere of 200 kPa above atmospheric pressure, the water was boiled up into the column until reflux was reached (135° C.). Deaerated acrylonitrile (containing 35 ppm MeHQ) was introduced at a feed point just below the catalyst bed at a rate of 48–152 g/hour, and water was fed into the column above the catalyst zone at such a rate as to produce the required product concentration. After the introduction of acrylonitrile, the temperature inside the catalyst bed decreased to the boiling point of the acrylonitrile-water azeotrope (about 104° C.). The product solution containing up to 50% by weight acrylamide (>98% conversion and selectivity) was removed from the reboiler at a rate of 200–500 g/hour.

EXAMPLE 4

In this example, the column set-up and catalyst packing were the same as for Example 3, but the nitrogen pressure inside the column was raised to 400 kPa above atmospheric pressure, which resulted in the reboiler temperature being 158° C. When the acrylonitrile (180 g/h) was introduced above the catalyst zone, the temperature in the catalyst zone decreased to 135°–145° C. and an aqueous solution of acrylic acid (about 75 g/h) and acrylamide (about 175 g/h) was produced.

EXAMPLE 5

Extrudates of a copper oxide catalyst in its reduced form (13.5 kg), supported in stainless steel wire socks and wrapped in demister wire, were packed in a 7 m section of a catalytic distillation column having dimensions of 10 m height×110 mm diameter. The bottom 2 m of the column was filled with 10 mm Berl saddles. De-aerated demineralized water was introduced into the reboiler to 50% capacity. Under a nitrogen atmosphere of 100 kPa above atmospheric pressure, the water was boiled up into the column until reflux was reached (121° C.). Deaerated acrylonitrile containing 35 ppm MeHQ was introduced at a feed point above the catalyst bed at a rate of 0.5–2.5 g/hour, and water was fed into the column above the catalyst zone at such a rate as to produce the required product concentration. After the introduction of acrylonitrile, the temperature inside the catalyst bed decreased to a boiling point of the acrylonitrile-water azeotrope (about 89° C.). The pH of the product solution was controlled between 5.0 and 6.0 by the addition of a 0.0125 M sulfuric acid solution into the reboiler. The product solution containing up to 50% by weight acrylamide (>98% conversion and selectivity) was removed from the reboiler at a rate of 5–30 kg/hour.

It is known to produce amides from nitriles by hydration of the nitriles in batch, fixed or slurry bed reactors. Three types of reactions are known, namely:

a) Homogeneous, mainly sulfuric acid, catalyzed reactions;

b) Heterogeneous catalyzed reactions with copper or copper based metal oxide mixtures, e.g. copper oxide or chromium oxide, as catalysts;

c) Reactions in which biocatalysts such as enzymes are used to facilitate the hydration of the nitriles.

These reactions are used for the production of amides, such as for the production of an acrylamide monomer from a nitrile such as acrylonitrile. Such monomers in turn are used for the production of water soluble polymers and copolymers which are used as mining flocculants, paper making aids, thickening agents, surface coatings and enhanced oil recovery products.

The Applicant is aware that in the mainly sulfuric acid catalyzed batch processes, the highly exothermic hydration reaction of nitriles is complicated by polymer formation, if the reaction temperature and reactant ratios are not controlled carefully. To end the reaction, the acid is neutralized, and this results in the production of an effluent comprising mainly sulfates contaminated with acrylamide. This necessitates the highly poisonous acrylamide having to be crystallized from the residual water and handled as a powder.

The Applicant is also aware that the processes involving heterogeneous catalytic reaction, are prone to polymerization and separation problems when slurry-bed technology is used, while low concentrations of acrylamide in water, in the order of 7%, only are produced when single fixed bed reactors, i.e. not a series of reactors, are used. Phase separation limits the quantity of acrylonitrile that may be fed to the reactor with water. In this case, the catalyst, unreacted acrylonitrile and water have to be removed by filtration and/or distillation to reach a desired concentration of about 50%. Apart from being uneconomical as regards energy utilization (heat is removed in the reaction step and added again at the distillation stage), these processes are highly capital intensive as several reactors and distillation towers are required for purification and concentration of the product. Catalyst life time is also limited although the catalyst may in some instances be regenerated by oxidation followed by reduction with hydrogen.

The Applicant has surprisingly found that by applying catalytic distillation technology to the hydration of amides, many disadvantage of the known processes can be eliminated. The process of the invention is a continuous process, enabling large savings in capital cost (typically one reaction vessel against five reaction vessels with known processes) with little or no effluent production. A further advantage is that the heat of the reaction is partly used to heat the reactants, implying lower energy requirements. Since catalytic distillation is essentially a distillation process, controlling the reaction temperature and thus preventing or inhibiting unwanted polymerization, poses no difficulties. The required concentration of the product (50%) can also be reached without additional separation processes, and catalyst life time is enhanced. Little or no unwanted polymerization is experienced since the product is constantly removed from the heat source. Thus, an aqueous solution of the product at the desired concentration (1%–60%) can be obtained directly from the reactor with no extra purification or concentration being required, while energy requirements are minimized. In the case of olefinic nitriles, oligomerization/polymerization poses no problem if the pH is controlled between 3 and 8 as the product is constantly removed from the heat source.

Olefinic amides, e.g. acrylamides, methacrylamide, crotonamide, and 3-butenamide, which are prepared by the process of this invention can be used as monomers in polymerization reactions. For example, non-ionic and anionic polyacrylamides have been produced from acrylamides prepared by the process of the invention. It is believed that it will also be possible to produce, by means of the process of the invention, acrylamide suitable for the production of cationic polyacrylamides.

The invention claimed is:

1. A process for producing an amide and/or acid from a nitrile, which process comprises introducing a nitrile, as a first reactant, and a hydration compound, as a second reactant which is capable of reacting with the nitrile to convert it to its corresponding amide thus hydrating the nitrile and/or to convert it to its corresponding acid, into a treatment zone in a column or tower, with the catalyst bed provided in a section of the tower, and with a distillation zone being provided above and below the catalyst bed and comprising at least one reaction zone in which the hydration reaction of the nitrile to the amide and/or acid takes place catalytically in the presence of a catalyst, and at least one distillation zone adjacent the reaction zone in which distillation of the reaction product(s) from the reaction zone and/or unreacted reactants, takes place, with the reaction zone comprising a packed bed of particles of a copper or copper-based hydration catalyst;

subjecting the nitrile to catalytic distillation in the treatment zone in the presence of the hydration compound, to hydrate at least some of the nitrile to the corresponding amide, the corresponding acid or mixtures thereof; and withdrawing the amide and/or acid from the treatment zone.

2. A process according to claim 1 wherein the first reactant comprises an unsaturated or aromatic nitrile which is thus hydrated to the corresponding unsaturated or aromatic amide and/or acid.

3. A process according to claim 1 or 2, which includes boiling a liquid component in a reboiling zone operatively connected to a lower end of the treatment zone, to provide the driving boiling force for the catalytic distillation, with a portion of the liquid component optionally being introduced into the treatment zone above or below the catalyst bed.

4. A process according to claim 3, wherein the liquid component is such that it is inert in the hydration reaction and only provides the driving force for the catalytic distillation, thus assisting in distillation of the reactants and products in the treatment zone, with the second reactant being fed into the treatment zone at a location spaced vertically along the treatment zone from the point of introduction of the first reactant into the treatment zone.

5. A process according to claim 4, wherein the second reactant is water and wherein the liquid component is an organic compound.

6. A process according to claim 3, wherein the liquid component and the second reactant are water, so that the liquid component reacts in the hydration reaction.

7. A process according to claim 1 or 2, wherein the higher boiling of the first and second reactants is introduced into the treatment zone above the catalyst bed, with the lower boiling thereof being introduced below the catalyst bed.

8. A process according to claim 1 or 2, which includes boiling a liquid component in a reboiling zone operatively connected to a lower end of the treatment zone, to provide the driving boiling force for the catalytic distillation, with a portion of the liquid component optionally being introduced into the treatment zone above or below the catalyst bed.

9. A process according to claim 1 or 2, wherein the higher boiling of the first and second reactants is introduced into the treatment zone above the catalyst bed, with the lower boiling thereof being introduced below the catalyst bed.

10. A process according to claim 9, wherein the higher boiling of the first and second reactants is introduced into the treatment zone above the catalyst bed, with the lower boiling thereof being introduced below the catalyst bed.

11. A process according to claim 4, wherein the higher boiling of the first and second reactants is introduced into the treatment zone above the catalyst bed, with the lower boiling thereof being introduced below the catalyst bed.

12. A process according to claim 5, wherein the higher boiling of the first and second reactants is introduced into the treatment zone above the catalyst bed, with the lower boiling thereof being introduced below the catalyst bed.

13. A process according to claim 6, wherein the higher boiling of the first and second reactants is introduced into the treatment zone above the catalyst bed, with the lower boiling thereof being introduced below the catalyst bed.

* * * * *